(12) United States Patent
Wang et al.

(10) Patent No.: US 7,173,021 B2
(45) Date of Patent: Feb. 6, 2007

(54) SYNTHESIS OF TEMOZOLOMIDE ESTERS AS POTENT ANTICANCER PRO-DRUGS FOR TOPICAL AND TRANSDERMAL APPLICATIONS IN TREATMENTS OF CANCERS

(75) Inventors: Yongfeng Wang, Birmingham (GB); Barbara R. Conway, Birmingham (GB); Panassaya Suppasansatorn, Bangkok (TH)

(73) Assignee: Tianjin North Pharm Sci-Tech Co., Ltd., Tianjin (CN)

( * ) Notice: Subject to any disclaimer, the term of this patent is extended or adjusted under 35 U.S.C. 154(b) by 0 days.

(21) Appl. No.: 11/074,037

(22) Filed: Mar. 7, 2005

(65) Prior Publication Data

US 2006/0047117 A1    Mar. 2, 2006

(30) Foreign Application Priority Data

Sep. 2, 2004    (CN) ........................ 2004 1 0068680

(51) Int. Cl.
C07D 487/04    (2006.01)
A61K 31/4188   (2006.01)
A61P 35/00     (2006.01)

(52) U.S. Cl. ..................... 514/183; 544/179
(58) Field of Classification Search ................ 544/179; 514/183
See application file for complete search history.

(56) References Cited

U.S. PATENT DOCUMENTS 5,260,291 A    11/1993    Lunt et al.

FOREIGN PATENT DOCUMENTS

| CN | 1485327   | * | 3/2004 |
| EP | 0 252 682 | * | 1/1988 |

OTHER PUBLICATIONS

West, Anthony R., Solid State Chemistry and its Applications, Wiley, New York, 1988, pp. 358 & 365.*
Cecil Textbook of Medicine, edited by Bennet, J.C., and Plum F., 20th edition,vol. 1, 1004-1010, 1996.*
Vippagunta et al., Advanced Drug Delivery Reviews 48: 3-26, 2001.*
Payne et al. Critical Reviews in Oncology/Hematology 53, 241-252, 2005.*
Wang et al., CN 1485327, CA 142: 392443, 2005.*
Beall, Howard D. and Sloan, Kenneth B.: International Journal of Pharmaceutics, *Topical delivery of 5-fluorouracil (5-FU) by 1,3-bisalkylcarbonyl-5-FU prodrugs*, vol. 231, pp. 43-49 (2002).
Bleehen, N. M., et al.: Journal of Clinical Oncology, *Cancer Research Campaign Phase II Trial of Temozolomide in Metastatic Melanoma*, vol. 13, No. 4, pp. 910-913 (Apr. 1995).
Bodor, N. and Sloan, K. B.: Department of Medicinal Chemistry, University of Florida, *Improved delivery through biological membranes XII. The effect of the incorporation of biphasic solubilizing groups into prodrugs of steroids*, pp. 235-250 (1982).
Bronaugh, Robert L. and Maibach, Howard I.: *in vitro percutaneous absorption*, Chapter 4, pp. 121-133.
*Transdermal Drug Delivery and Delivery Systems*, Chapter 7, pp. 301-380.
Diez-Sales, O., et al.: International Journal of Pharmaceutics, *The prediction of percutaneous absorption: I. Influence of the dermis on in vitro permeation models*, vol. 100, pp. 1-7 (1993).
Gajewski, Thomas F.: Journal of Clinical Oncology, *Temozolomide for Melanoma: New Toxicities and New Opportunities*, vol. 22, No. 4, pp. 580-581 (Feb. 15, 2004).
Heimberger, Amy B., et al.: Clinical Cancer Research, *Temozolomide Delivered by Intracerebral Microinfusion is Safe and Efficacious Against Malignant Gliomas in Rats*, vol. 6, pp. 4148-4153 (Oct. 2000).
Flynn, Gordon L., et al.: In Vitro Transport, *Transdermal Delivery of Drugs*, Chapter 4, vol. 1, pp. 45-59; and Wester, Ronald C. and Malbach, Howard I: Animal Models for Transdermal Delivery, Chapter 5, vol. 1, pp. 61-83.
Hotchkiss, Sharon A. M.: Imperial College School of Medicine, London, England, *Dermal Metabolism*, Chapter 2, pp. 43 to 101.
Hotchkiss, Sharon A. M.: Imperial College School of Medicine, London, England, *Skin as xenobiotic metabolizing organ*, Chapter 6, pp. 217-262.
Behrendt, H. and Kampffmeyer, H. G.: XENOBIOTICA, *Absorption and ester cleavage of methyl salicylate by skin of single-pass perfused rabbit ears*, vol. 19, No. 2, pp. 131-141 (1989).

(Continued)

Primary Examiner—Venkataraman Balasubramanian
(74) Attorney, Agent, or Firm—Todd E. Garabedian; Elizabeth A. Galletta; Wiggin and Dana LLP (57) ABSTRACT

This invention relates to the use of temozolomide esters (4-dihydro-3-methyl-4-oxoimidazo[5,1-d]-1,2,3,5-tetrazine-8-carboxylate esters) Formula 1 as potent anticancer pro-drugs for treatment of cancers by topical and transdermal applications, and to a novel process for synthesis of temozolomide esters by a direct esterification of temozolomide acid (3,4-dihydro-3-methyl-4-oxoimidazo[5,1-d]-1,2,3,5-tetrazine-8-carboxylic acid) with a halogeno-aliphatic compound in presence of a base, or with an alcohol in presence of a dehydrate agent

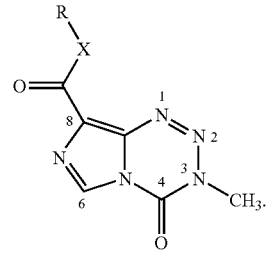

Formula 1

9 Claims, 5 Drawing Sheets

OTHER PUBLICATIONS

Lopez, A., et al.: International Journal of Pharmaceutics, *Skin permeation model of phenyl alcohols: comparison of experimental conditions*, vol. 173, pp. 183-191 (1998).

Maenpaa, Juhani, et al.: Cancer Chemotherapy and Pharmacology, *Topical toremifene: a new approach for cutaneous melanoma?*, vol. 32, pp. 392-395 (1993).

Middleton, M. R., et al.: Journal of Clinical Oncology, *Randomized Phase III Study of Temozolomide Versus Dacarbazine in the Treatment of Patients With Advanced Metastatic Malignant Melanoma*, vol. 18, No. 1, pp. 158-166 (Jan. 2000).

Mosmann, Tim: Journal of Immunological Methods, *Rapid Colorimetric Assay for Cellular Growth and Survival: Application to Proliferation and Cytotoxicity Assays*, vol. 65, pp. 55-63 (1983).

Rathbone, D. L., et al.: Journal of Pharmaceutical Pharmacology, *Soluble prodrugs of the anticancer drugs temozolomide and mitozolomide*, Appendix I, vol. 51 (Supplement), No. 26, p. 111 (1999).

Raymond, Eric, et al.: Clinical Cancer Research, *Activity of Temozolomide against Human Tumor Colony-Forming Units*, vol. 3, pp. 1759-1774 (Oct. 1997).

Sampson, John H., et al.: Clinical Cancer Research, *Treatment of Neoplastic Meningitis with Intrathecal Temozolomide*, vol. 5, pp. 1183-1188 (May 1999).

Soe, Lin, et al.: Cancer Chemotherapy and Pharmacology, *Tissue distribution of transdermal toremifene*, vol. 39, pp. 513-520 (1997).

Stevens, Malcolm F. G., et al.: Journal of Medicinal Chemistry, *Antitumor Imidazotetrazines...*, vol. 27, No. 2, pp. 196-201 (1984).

Stevens, Malcolm F. G., et al.: Cancer Research, *Antitumor Activity and Pharmacokinetics of CCRG 81045*, vol. 47, pp. 5846-5852 (Nov. 15, 1987).

Su, Y. B., et al.: Journal of Clinical Oncology, *Selective CD4+ Lymphopenia in Melanoma Patients Treated With Temozolomide: A Toxicity With Therapeutic Implications*, vol. 22, No. 4, pp. 610-616 (Feb. 15, 2004).

Tsang, Lincoln L. H., et al.: Cancer Chemotherapy and Pharmacology, *Comparison of the cytotoxicity in vitro of temozolomide and dacarbazine, prodrugs of 3-methyl-(triazen-I-yl)imidazole-4-carboxamide*, vol. 27, pp. 342-346 (1991).

Tsang, Lincoln L. H., et al.: Cancer Chemotherapy and Pharmacology, *Characterization of urinary metabolites of temozolomide in humans and mice and evaluation of their cytotoxicity*, vol. 26, pp. 429-436 (1990).

Valia, Kirti H., et al., Drugs Development and Industrial Pharmacy, *Long-Term Permeation Kinetics of Estradiol: (III) Kinetic Analyses of the Simultaneous Skin Permeation and Bioconversion of Estradiol Esters*, vol. 11, No. 6&7, pp. 1133-1173 (1985).

Wang, Yongfeng, et al.: Journal of Organic Chemistry, *Antitumor Imidazotetrazines. 35. New Synthetic Routes to the Antitumor Drug Temozolomide*, vol. 62, pp. 7288-7294 (1997).

Leo, Albert, et al.: Chemical Reviews, *Partition Coefficients and Their Uses*, vol. 71, No. 6, pp. 525-554 (Dec. 1971).

* cited by examiner

SYNTHESIS OF TEMOZOLOMIDE ESTERS AS POTENT ANTICANCER PRO-DRUGS FOR TOPICAL AND TRANSDERMAL APPLICATIONS IN TREATMENTS OF CANCERS

BACKGROUND OF THE INVENTION

Temozolomide is an alkylating agent that has displayed pre-clinical activity against a broad spectrum of murine tumours in vivo (Stevens M G F, 1987). In vitro studies have demonstrated activity against a wide variety of tumours including some usually resistant to chemotherapy with more established drugs (Raymond E, 1997). It is currently indicated for the treatment of malignant glioma and is available as a capsule for oral administration in a number of countries including US and Europe. Phase II trials of temozolomide have confirmed that it has significant activity in patients with metastatic malignant melanoma (Bleehen N M, 1995). More recently, a phase III trial indicated that temozolomide is as effective as dacarbazine in patients with advanced metastatic melanoma with progression-free survival favouring temozolomide (Middleton M R, 2000). Prolonged exposure, using an extended dosing schedule, has been suggested to increase clinical activity but has led to an unusually high level of side-effects. Major side-effects of temozolomide include leukopenia, nausea, vomiting with alopecia, rash and constipation to a lesser degree. With extended dosing, there was also an increased incidence of opportunistic infections. In addition, temozolomide has been shown to have dose-limiting myelotoxicity following oral delivery. Therefore, it is very important to develop other potential routes of delivery to maximize temozolomide therapeutical potential. However, poor solubility in both aqueous and organic media and instability of the solubilised form, have resulted in serious difficulties for pharmaceutical studies and exploration of alternative delivery routes. As a result, only a limited number of studies have been carried out with attempts to reduce the toxicity via intrathecal delivery of a solubilised formulation (Sampson J. H, 1999) and intracerebral microinfusion of temozolomide (Heimberger A. M, 2000)

The development of new therapeutic agents and new drug delivery strategies is of very important for treating cancers. Skin cancers (melanomas) are one of most difficult to treat cancers because they are very aggressive and resistant to general chemotherapy. In order to maximise temozolomide efficiency and to improve its therapeutic benefit for curing skin cancer, particularly in the early stages, transdermal delivery may fulfill the object. It has been showed that topically applied toremifene, an oestrogen-receptor antagonist licensed for treatment of breast cancer, achieved high local concentrations of drug in the tumours, with low systemic levels when investigated as a melanoma treatment (Maenpaa, J, 1993 and Soe L, 1997). Dermal delivery of drugs is greatly limited by the efficient skin barrier and the generally unfavourable physicochemical properties of drugs. Synthesis of an ester prodrug is one method to enhance the skin absorption of a topically applied drug where, by chemical modification of the penetrating molecule, its delivery can be enhanced. The epidermal layer contains many non-specific enzymes that are capable of hydrolysing carboxylate bonds to release the parent compound (Valia K. H. 1985). An example of such an approach is the esterification of poorly skin-permeable estradiol to form lipophilic estradiol esters. The study showed that all the estradiol esters investigated were extensively metabolised in the skin during permeation to regenerate the biologically active parent. Some esters were shown to achieve permeation rates two-to-four fold higher than free estradiol. A series of 1,3-bisalkylcarbonyl-5-flurouracil prodrugs have been investigated for topical delivery (Beall H D, 2002).

Temozolomide spontaneously degrades in physiological fluid to generate the cytotoxic methylating agent, 5(3-methyl-1-triazeno) imidazole-4-corboxamide, which subsequently fragments to the DNA-methylating agent, methyldiazonium. Tsang (Tsang, L L H 1990) in his study of urinary metabolites of temozolomide described in vitro $IC_{50}$ of 8-(carboxylic acid)-3-methylimidazo[5,1-d]-1,2,3,5-tetrazine-4(3H)-one (temozolomide acid) was almost identical to that of temozolomide against TLX5 lymphoma cell line. In light of this report, we decided to conduct experiments to verify whether or not the temozolomide acid is as active as temozolomide against melanoma and glioma. In in vitro bioactivity tests, the temozolomide acid was used against a selected panel of cancer cell lines including melanoma and glioma. The experiments demonstrated the temozolomide acid is cytotoxic against certain melanoma and glioma cells and the $IC_{50}$s of the temozolomide acid and temozolomide are in the same grade. Therefore, the temozolomide acid is the parental active drug with the same indications to temozolomide and the temozolomide ester prod-rug approach is the feasible strategy for maximizing temozolomide therapeutic benefit for the treatments of cancers, particularly for skin cancer through topical or transdeermal application.

The past studies of structural optimization of temozolomide mainly concentrated on modification of an alkyl group on N3 and an alkyl group on N of 8-carbamoyl. Though the general formula of EP 0252682 covered temozolomide methyl, ethyl, propyl and butyl esters, no synthetic methods and physical and chemistry data for these esters were included, except a benzyl ester. U.S. Pat. No. 5,260,291, GB 2104522, GB 2125402, FR 2511679 and FR 2531958 only covered temozolomide and its 8-carboxylamide derivatives. Temozolomide ethyl ester was reported as a precursor for studies of new synthetic routes for temozolomide (Wang Y, 1997).

In conclusion, neither a research aiming to develop a topical or a transdermal administration of temozolomide and its derivatives through design and synthesis of a series of temozolomide esters nor a general synthesis for temozolomide esters have been reported. Furthermore, there is no report about enzymatically metabolizing temozolomide esters into the bioactive temozolomide acid in skins and potential application of the temozolomide esters as pro-drugs in treating cancers.

SUMMARY OF THE INVENTION

According to the present invention, there is provided a homologous series of pro-drug temozolomide ester derivatives and a novel synthetic method, a direct esterification of temozolomide acid with a halogeno-aliphatic compound or with an alcohol. The temozolomide esters, which efficiently penetrate through skins wherein are metabolized into the bioactive temozolomide acid, are new pharmaceutical useful compounds, particularly as potent anticancer pro-drugs for topical and transdermal applications in treatment of skin cancers.

DETAILED DESCRIPTION OF THE INVENTION

The present invention provides a series of 3,4-dihydro-3-methyl-4-oxoimidazo[5,1-d]-1,2,3,5-tetrazine-8-carboxylate esters (the temozolomide esters) as anticancer prodrugs. The present invention also provides a general and applicable synthetic method for preparation of temozolomide esters in pure and bulky form: the direct esterification of 3,4-dihydro-3-methyl-4-oxoimidazo[5,1-d]-1,2,3,5-tetrazine-8-carboxylic acid (temozolomide acid) with a halogeno-aliphatic compound in presence of a base or with an alcohol in presence of a dehydrate agent. The present invention demonstrates the temozolomide acid and the temozolomide hexyl ester are as substantially as cytotoxic as temozolomide against certain melanoma and glioma cells in vitro. Furthermore, the present invention depicts, in comparison with temozolomide, the temozolomide esters efficiently permeate through skins and are metabolized into bioactive temozolomide acid. Finally the present invention demonstrated that, through topical application, temozolomide hexyl ester effectively inhibits tumour growth in the mice which are inoculated with human skin tumour. Therefore the temozolomide esters are potent anticancer prodrugs, particularly for topical and transdermal applications in treatment of skin cancers.

The temozolomide esters are generally of the formula:

where X is O (oxygen) and S (sulphur); and R is a $C_4$–$C_{10}$ alkyl, cycloalkyl, alkenyl or alkynyl group, each of the groups being optionally substituted by one or more substituent groups independently selected from halogen atoms, —$OR_1$, —$SR_1$, —$NR_1R_2$, and an optionally substituted phenyl group.

$R_1$ and $R_2$ each independently represent a hydrogen atom, or a $C_1$–$C_{10}$ alkyl, cycloalkyl, alkenyl or alkynyl group.

Preferably R is a $C_4$, $C_5$, $C_6$, $C_7$, $C_8$, $C_9$ or $C_{10}$ compound, especially a $C_6$ compound.

$R_1$ and $R_2$ may be a $C_1$, $C_2$, $C_3$, $C_4$, $C_5$, $C_6$, $C_7$, $C_8$, $C_9$ or $C_{10}$ compound.

The cytotoxicity of the temozolomide acid was assessed in vitro against a selected panel of cancer cell lines including human melanoma and glioma cells in comparison with temozolomide. The experiments demonstrated the temozolomide acid is as active as temozolomide against certain melanoma and glioma cells. The results are summarized in Table 1 and Table 2 from two separated experiments. Therefore, the temozolomide acid is the active drug with the same indications to temozolomide and the temozolomide acid can serve as the parental drug in the ester prodrug approach for maximizing temozolomide therapeutic benefit for the treatments of cancers, particularly for skin cancer through topical or transdermal application.

TABLE 1

In vitro cytotoxicity of the temozolomide acid and the temozolomide hexyl ester in comparison with fluorouracil against cancer cells

| Compounds | $IC_{50}(\mu g/ml)$[a] | | | | | |
|---|---|---|---|---|---|---|
| | MV3 | MCF-7 | Bel-7402 | A549 | HCT-8 | BGC-823 |
| The temozolomide hexyl ester | 8.835 | 19.995 | 27.203 | 26.632 | 28.644 | >19.5 |
| The temozolomide acid | 14.625 | 14.911 | 16.957 | >19.5 | 18.525 | >19.5 |
| Fluorouracil | 0.427 | 0.629 | 0.495 | 0.126 | 0.606 | 0.722 |

[a]Mean ± SEM for at least three determinations.

TABLE 2

In vitro cytotoxicity of the temozolomide acid, the temozolomide hexyl ester and temozolomide, in comparison with darcabazine and carmustine against cancer cells[a]

| Compound | IC$_{50}$(μg/ml)[a] | | | | | | |
|---|---|---|---|---|---|---|---|
| | MV3 | M14 | B16 | B16-BL6 | TJ899 | SHG-44 | TJ905 |
| The temoolomide hexyl ester | 25.000 | >100 | 28.261 | >100 | >100 | 9.459 | >100 |
| The temozolomide acid | 36.047 | 99.020 | 36.170 | 43.500 | >100 | 7.067 | >100 |
| Temozolomide | 7.860 | >100 | 61.905 | >100 | >100 | 9.043 | >100 |
| Darcabazine | 0.647 | 0.558 | 10.000 | 61.765 | 5.600 | 1.261 | 6.860 |
| Carmustine | 6.354 | 28.696 | 7.752 | 13.111 | 54.211 | 7.196 | 67.308 |

[a]Mean ± SEM for at least three determinations.

The generally used methods for syntheses of carboxylate esters include two steps. Firstly, the carbonyl group in a carboxylic acid is activated through forming an acid chloride or an active ester, followed by acylation with an alcohol. These approaches have been used in the synthesis of imidazotetrazinone derivatives and were found expensive and low yield. In the present invention, temozolomide esters are synthesised by the direct esterification between temozolomide acid and a halogeno-aliphatic compound in presence of a base. The halogeno-alphatic compounds include chloro, bromo and iodo-alphatic compounds and the base include organic and inorganic base, particularly organic amines: (1) metal organic amine bases, such as LDA (lithium diisopropylamide), K-HMDS (potassium hexamethyldisilazane), LiTMP (Lithium 2,2,6,6-tetramethylpiperidide), (2) alkylamine, such as di- and trialkylamine, Hünig's Base (N-ethyl di-isopropylamine), urea, guanidine, (3) aromatic amines such as aniline, diphenylamine, p-dimetylaminoaniline, 2,6-dimethylpyridine, DMAP (4-dimethylaminopyridine), proton sponge, (4) heterocyclic amines such as, aziridine, indoles, imidazole, morphines, pyridines, pyrroles, pyrazines, pyrazoles, tetrahydropyrroles, DABCO (1,4-diazabicyclo[2.2.2]octane), DBN (1,5-diazabicyclo[4.3.0]non-5-ene), DBU (1,8-diazabicyclo[5.4.0]undec-7-ene)[Scheme 1]. In the present invention, temozolomide esters are also synthesised by the direct esterification between temozolomide acid and an alcohol in the presence of one dehydrate agents of DCC (1,3-dicyclohexylcarbodiimide), BOP (benzotriazole-1-yl-oxy-tris(dimethylamino)-phosphonium-hexafluorophosphate), PyBrOP (bromo-tris-pyrrolidino-phosphonium hexafluorophosphate), HBTU (2-(1H-benzotriazole-1-yl)-1,1,3,3-tetramethyluronium hexafluorophosphate), TBTU (2-(1H-benzotriazole-1-yl)-1,1,3,3-tetramethyluronium tetrafluoroborate), TNTU (2-(5-norbornene-2,3-dicarboximido)-1,1,3,3-tetramethyluronium tetrafluoroborate), TSTU (O—(N-succinimidyl)-1,1,3,3-tetramethyluronium tetrafluoroborate), and HOBt (N-hydroxybenzotriazole), The synthetic methods in the present invention are less in steps, easier to perform, cost effective and high yields.

Scheme 1.
Synthetic sequence for temozolomide ester and amide derivatives

The potential of temozolomide esters used as topical and transdermal prodrugs is first proven through studies of their solubility. That is a decreased trend of solubility in an aqueous solution with increase of the length of the ester hydrocarbon alkyl chain of the temozolomide esters. The studies were carried out by using of 10% v/v propylene glycol (PG) aqueous solution and the results are summarised in Table 3. It is clear the solubility constantly decreases from the methyl ester to the octyl ester, while temozolomide itself is 3.0 mg/ml similar to that of the methyl ester. This indicates that extending the length of the ester alkyl chain by CH$_2$ renders a significant affect on the lipophilicity of the temozolomide esters. Similarly to the esters, the solubility of the temozolomide amide products in the aqueous solution is considerably lower than that of temozolomide.

TABLE 3

Solubility of temozolomide and its ester derivatives
in 10% v/v propylene glycol under ambient conditions

| Compound | Concentration (mg/ml) |
| --- | --- |
| Temozolomide | 3.0 |
| Temozolomide methyl ester | 3.0 |
| Temozolomide ethyl ester | 2.5 |
| Temozolomide n-propyl ester | 2.0 |
| Temozolomide n-butyl ester | 1.4 |
| Temozolomide n-hexyl ester | 0.4 |
| Temozolomide n-octyl ester | 0.3 |
| Temozolomide isopropyl amide | 2.8 |
| Temozolomide n-butyl amide | 1.8 |
| Temozolomide sec-butyl amide | 1.8 |
| Temozolomide t-butyl amide | 1.4 |

Log P values of temozolomide (1) and the temozolomide esters were calculated using TSAR (Oxford Molecular, Oxford, UK), Molecular Modeling Pro (ChemSW, Fairfield, Calif.) and Chem Office 7.0 (CambridgeSoft, Cambridge, UK) programmes. Calculated Log P values were verified for temozolomide and the temozolomide hexyl ester by measuring the octanol/water coefficient (Table 4). The measured log P value for temozolomide is −0.66, while the measured log P value for the temozolomide hexyl ester is 2.56, the desired log P value of a drug for a topical and transdermal applications.

TABLE 4

Calculated and measured log P values for temozolomide
1 and the temozolomide esters

| Compound | Formula | cLog P[a] | cLog P[b] | cLog P[c] | mLog P[d] |
| --- | --- | --- | --- | --- | --- |
| temzolomide | $C_6H_6N_6O_2$ | −0.07 | −1.13 | −0.33 | −0.66 |
| methyl ester | $C_7H_7N_5O_3$ | 0.82 | −0.40 | 0.58 | |
| ethyl ester | $C_8H_9N_5O_3$ | 1.17 | −0.06 | 0.92 | |
| propyl ester | $C_9H_{11}N_5O_3$ | 1.63 | 0.41 | 1.40 | |
| butyl ester | $C_{10}H_{13}N_5O_3$ | 2.03 | 0.81 | 1.82 | |
| hexyl ester | $C_{12}H_{17}N_5O_3$ | 2.82 | 1.60 | 2.66 | 2.56 |
| octyl ester | $C_{14}H_{21}N_5O_3$ | 3.62 | 2.39 | 3.49 | |

[a]Calculated log P (cLog P) from TSAR;
[b]cLog P from MMP;
[c]cLog P from Chem office 7.0;
[d]measured Log P (mLog P) from the octanol/water system.

Esterases are a diverse group of phase I metabolising enzymes. These enzymes mediate reactions involved in the hydrolysis of acid esters to a free acid and an alcohol. It has been established that the skin possesses considerable esterase activity (Hotchkiss, 1992), and this property has been exploited in the development of pro-drugs that require activation by skin esterases (Higuchi and Yu, 1987). Pro-drugs such as ester derivatives are generally highly lipophilic compounds compared to their predecessors. The hydrophobic pro-drugs can readily partition into the skin, where they are metabolised by esterase enzymes, and transformed to the active free acid form. To ensure the existence of esterase enzymes within the skin, esterase enzyme inhibitor studies have been conducted to examine the effect on the hydrolysis of a salicylic acid diester (Hotchkiss, 1992). In the absence of inhibitors, the diester is completely hydrolysed to the monoester and finally to salicylic acid in mouse and human skin. The addition of inhibitors was seen to inactivate esterase enzyme activity within the skin.

Additionally, several permeation studies have demonstrated that many esters products such as corticosteroid (Higuchi and Yu, 1987), salicylate (Kampffineyer H. G, 1989), and oestradiol (Valia et al., 1985) can be extensively hydrolysed, transformed into the free acid form, whenever there is an esterase enzyme within the skin.

Figure 1:
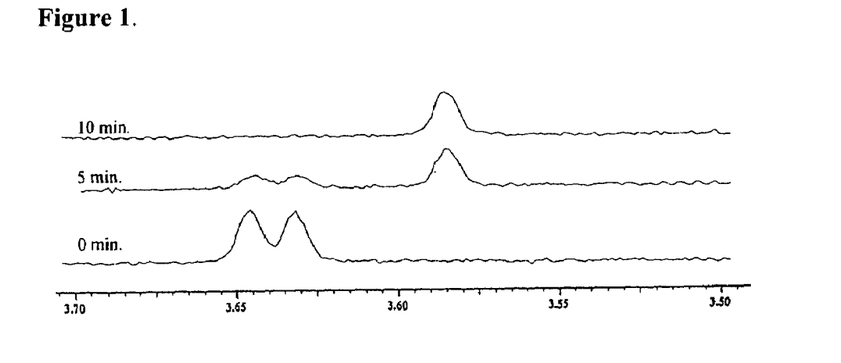
FIG. 1 $^1$H NMR spectra 1 for the degradation profile of the temozolomide methyl ester under incubation condition.

First the present invention establishes the metabolised process of the temozolomide esters by pig liver esterase in vitro. $^1$H NMR spectra 1 (FIG. 1) records the degradation profile of the temozolomide methyl ester under incubation condition (Rathbone D L, 1999). At time 0 minute, the resonance frequencies of the two singlets at 3.63 and 3.65 ppm, responding for the two methyl groups in the temozolomide methyl ester molecule, suggests the methyl ester is un-attacked. After 5 minutes, the singlet at 3.58 ppm, corresponding to N3-methyl of the temozolomide acid, indicates the presence of temozolomide acid; while the intensities of the two singlets at 3.63 and 3.65 ppm are proportionally reduced. Finally, at 10 minutes, the intensity of the singlet at 3.58 ppm grows to the grade similar to the original of the two singlets at 3.63 and 3.65 ppm, which while are completely eliminated. This result clearly demonstrates that methyl ester has been completely degraded and released temozolomide acid when it exposed to pig liver esterase enzyme. In contrast, under the same condition the temozolomide n-butyl amide gradually decomposed into un-identifiable products without the observation of temozolomide acid after 8 hours incubation. This discovery establishes the solid foundation for the temozolomide esters to be considered as the potential anticancer pro-drugs.

In vitro techniques are widely used in the assessment of topical and transdermal absorption. The major advantages of in vitro investigations are (1) the experimental conditions are controllable, (2) absorption rates and skin metabolism are accurately measurable without interference from systemic metabolic processes. Thus, the in vitro results are the fundamental data for selecting the compounds for in vivo studies. Numerous experiments demonstrate good correlations between in vitro and in vivo percutaneous absorption. For example, a recent review by Bronaugh and Maibach (1987) details experiments reporting a similarity between in vivo and in vitro absorption measurement with tributyl phosphate in rat, rabbit, and pig skin.

In the present invention, first a purely lipophilic synthetic silicone membrane, which behaves as the skin principal barrier (stratum corneum) is used in in vitro study of permeation profiles of the temozolomide esters because the experiment provides an excellent preliminary interpretation of the compound skin permeating ability, followed by studies with full-thickness rat skins. Based on these results, the temozolomide hexyl ester, the temozolomide butyl amide and temozolomide are studied in human skin. The experiments are completed by using Franz diffusion cell (FIG. 2) and proves that the temozolomide esters posses superior skin permeating ability to temozolomide and the temozolomide amides, and the temozolomide esters are readily metabolized into bioactive temozolomide acid by enzymes in rat and human skins. Finally, the temozolomide hexyl ester is applied on BALB/c nude mice inoculated with human melanoma MV3. In a period of two week experiments, the temozolomide hexyl ester effectively inhibits the growth of MV3 melanoma in the mice. The inhibition rate of the tumour growth is 80.5%. All these results demonstrate that the temozolomide esters are potential anticancer pro-drugs, particularly for topic and transdermal applications.

Figure 3:
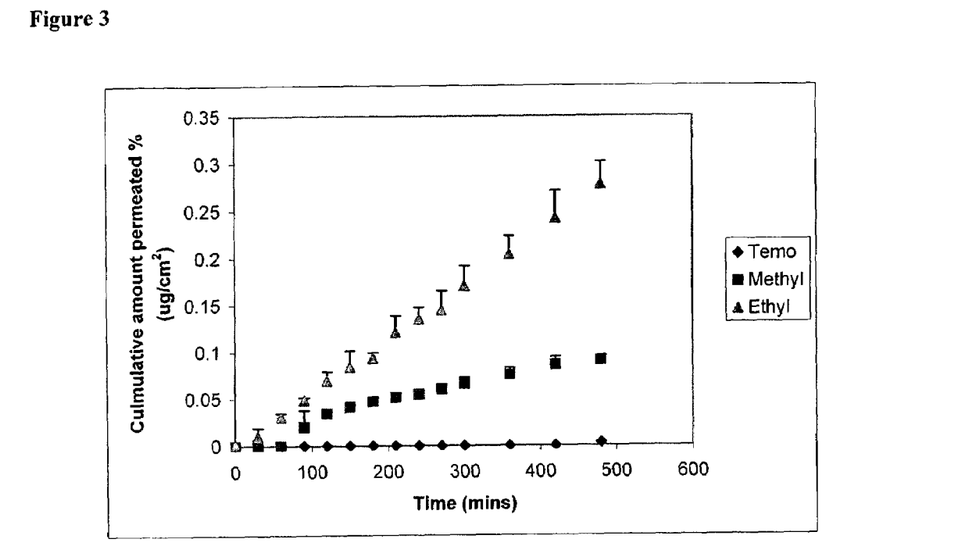
FIG. 3 describes permeations of temozolomide, temozolomide methyl and ethyl esters through synthetic silicone membrane.
Figure 4:
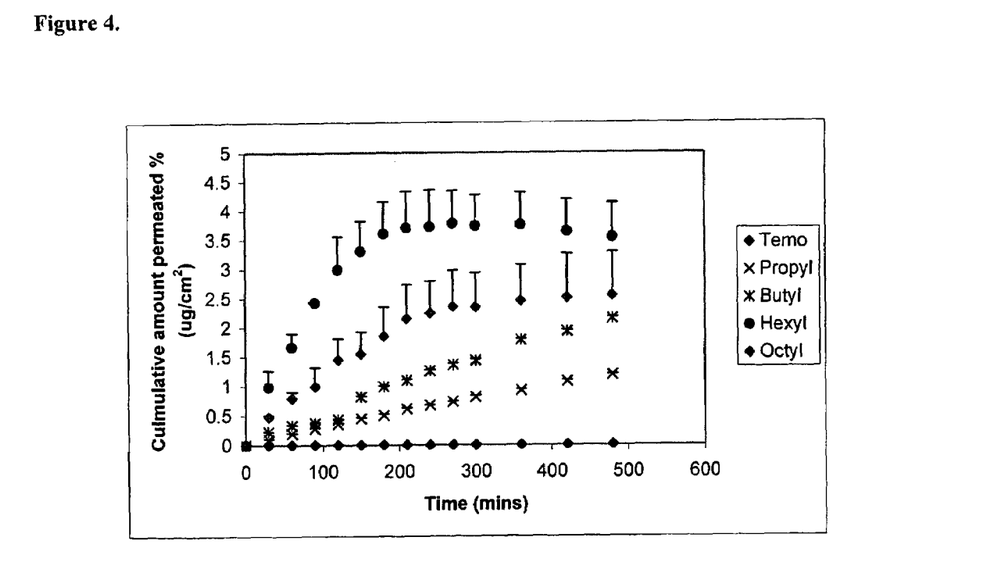
FIG. 4 depicts permeations of temozolomide, temozolomide propyl, butyl, hexyl and octyl esters through synthetic silicone membrane.

FIGS. 3 and 4 show the permeability characteristics of the temozolomide esters and temozolomide via lipophilic synthetic silicone membrane. It is clearly that temozolomide, its methyl and ethyl esters can not pass through the synthetic membrane easily (FIG. 3); in contrast, its n-propyl, n-butyl, n-hexyl, and n-octyl esters can passed through the membrane far more efficiently (FIG. 4). These results can be explained by considering the increase of the lipophilicity with the increase of the ester alkyl chain length from the methyl ester to the octyl ester, because generally for a organic compound the more $CH_2$ it has the more lipophilic it behaves. It is noticed that the permeability of the octyl ester is significantly less than the hexyl ester though the former has more $CH_2$. This could be caused by two main factors, one is the size of the molecule and another is a stronger interaction between the octyl ester with the membrane. For small size molecules (molecular weight<1000 daltons), the effect of size on the diffusion (D) in liquids may be viewed in terms of the following Stokes-Einstein equation in which M is molecular weight and C is constant:

$$D = C \cdot M^{-1/3}$$

From Stokes-Einstein equation, it is clear that higher molecular weight leads to lower diffusion of molecules. However, this may not be the main reason because for the rest of the esters, molecular weight seems to have less of an effect. Therefore, the higher lipophilic affinity between the octyl ester and the synthetic silicone membrane may be the major factor for causing the lower permeation.

This result indicates that there is an optimum lipophilicity for the temozolomide esters to maximize their permeation through the synthetic silicone membrane and this optimum lipophilicity is determined by the components of the ester alkyl groups in the temozolomide esters. In these experiments the alkyl groups in the temozolomide esters are higher or lower than $C_6$ results in lower permeations than the maximum. The literature has reported similar observations, for examples, the optimum flux ($J_s$) of alkanols in aqueous solution across an isolated epidermis was found at hexanol ($C_6$) (Chien, 1992), and Diez-Sales et al. (1993) also reported that the optimal permeability coefficient value for aniline corresponds to 4-n-butyl aniline through full-thickness rat skin, as well as the report of that for phenol compounds to permeate through rat skin, an optimum permeability coefficient value is at 5-phenyl pentanol (Lopez et al., 1998).

Figure 5:
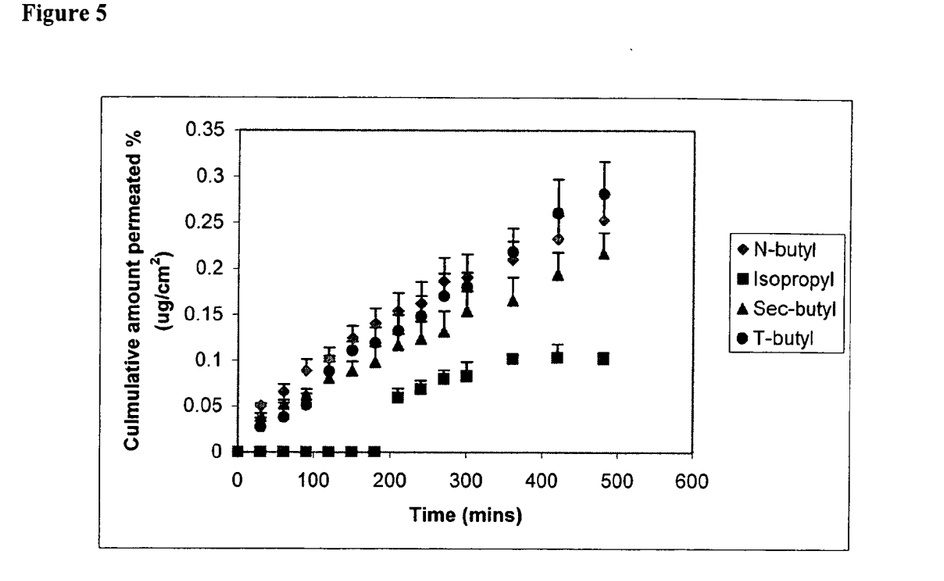
FIG. 5 depicts permeation of temozolomide, temozolomide isopropyl, n-butyl, sec-butyl and t-butyl amides through synthetic silicone membrane.

FIG. 5 describes the comparison of the permeability of temozolomide and its amide derivatives through the synthetic silicone membrane. It can be seen temozolomide has the lowest permeation, and the butyl amide is better than the isopropyl amide same to the observations in the temozolomide esters: the longer alkyl carbon chain the higher permeation. These results are also in line with the solubility data as the butyl amides are more lipophilic than the isopropyl amide. The difference in constitutional isomers (straight and branched chains) of butyl amide products was also investigated and was expected to indicate differences in permeation. Butane and isobutane are different compounds with different properties. For example, the boiling point of butane is $-0.5°$ C., whereas that of isobutane is $-11.7°$ C. (Loudon, 1995). However, they have the same molecular formula, $C_4H_{10}$. Therefore, attaching different constitutional isomers to the parent molecule is likely to indicate different properties. However, the results suggest that the differences in constitutional isomers do not significantly change the permeability characteristics. This probably indicates that the differences of constitutional isomers do not alter much of the lipophilic properties of these compounds.

Figure 6:
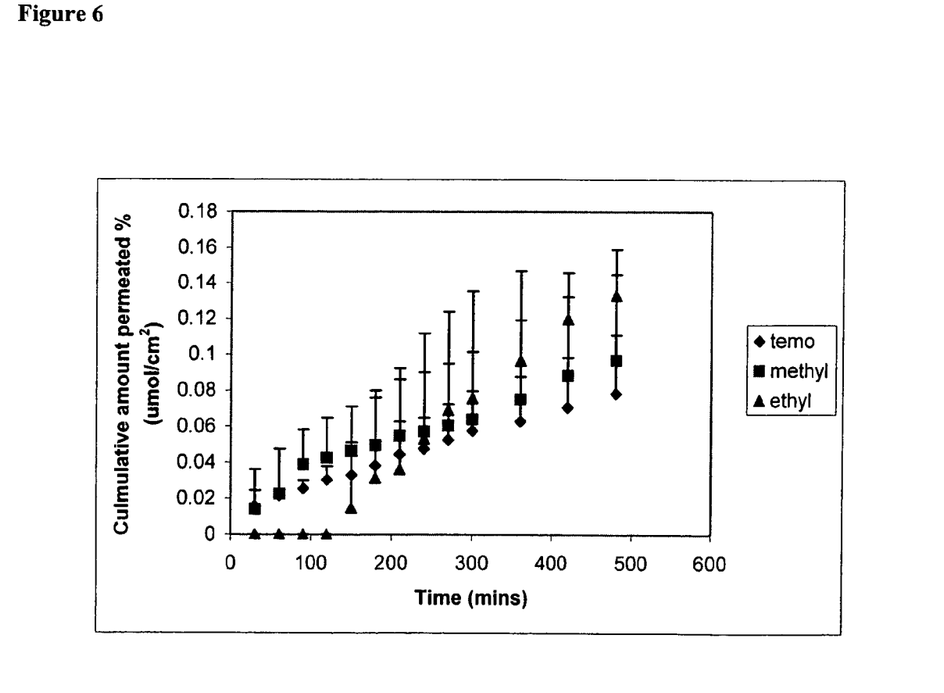
FIG. 6 depicts permeation of temozolomide, temozolomide methyl and ethyl esters through full-thickness rat skin.
Figure 7:
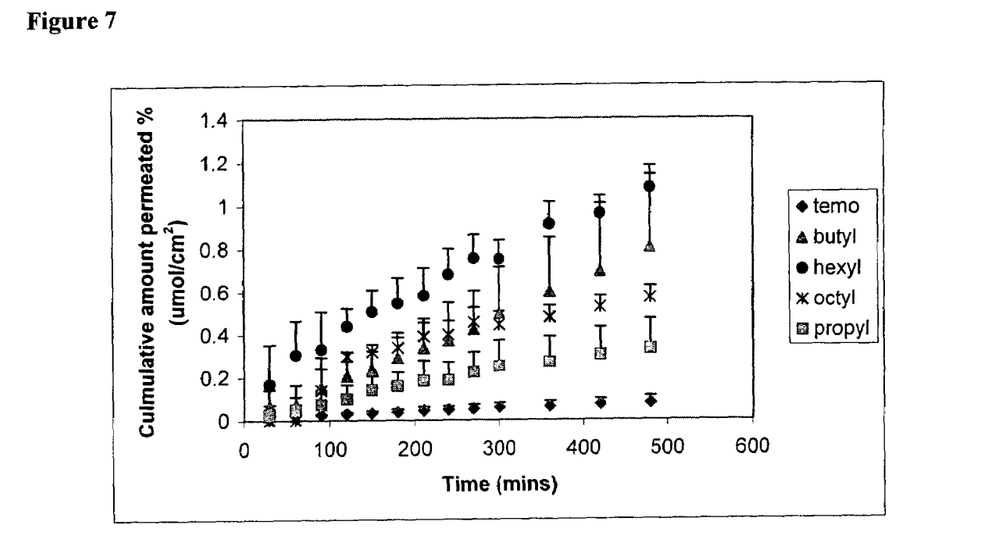
FIG. 7 depicts permeation of temozolomide, temozolomide n-propyl, n-butyl, n-hexyl and n-octyl esters through full-thickness rat skin.

FIGS. 6 and 7 illustrate the permeation of the temozolomide esters and temozolomide through whole rat skin. It is clear that the results are similar to those of the experiment with the synthetic silicone membrane. Again, the alkyl groups of the esters consisted of 3 to 8 —$CH_2$— fragments results in increased permeations through the rat skin (FIG. 7) and as the alkyl chain length increases, the cumulative amount permeated (%) increases to a maximum value at $C_6$ (the hexyl ester, FIGS. 7 and 8). These results indicate that the hexyl ester posses an intrinsic balance between the permeability and lipophilicity with the rat skin, which renders it a maximized permeation. As expected, all the temozolomide esters are detected in the temozolomide acid form. This finding demonstrates that the temozolomide esters are metabolized by esterase enzymes within the rat skin, and the esters are potent anticancer pro-drugs. These results are similar to reported corticosteroid esters which were rapidly hydrolysed to the free corticosteroid acid (i.e. betamethasone, prednisolone, and triamsinolone) in animal and human skin (Hotchkiss, 1988). Under the same conditions, the temozolomide amides also studied. However, we observe during the experiment with the rat skin the temozolomide amides degrades and after 8 hours there is no temozolomide acid is detected in the reception cells. By using the same HPLC condition for temozolomide acid, two overlapped peaks display on the chromatogram, none of which is respond for the temozolomide acid and temozolomide. This seems that the amides undergo bioconversion (i.e. by hydrolytic or enzymatic transformation) within viable rat skin and transform to a metabolite that is not temozolomide acid.

Figure 8:
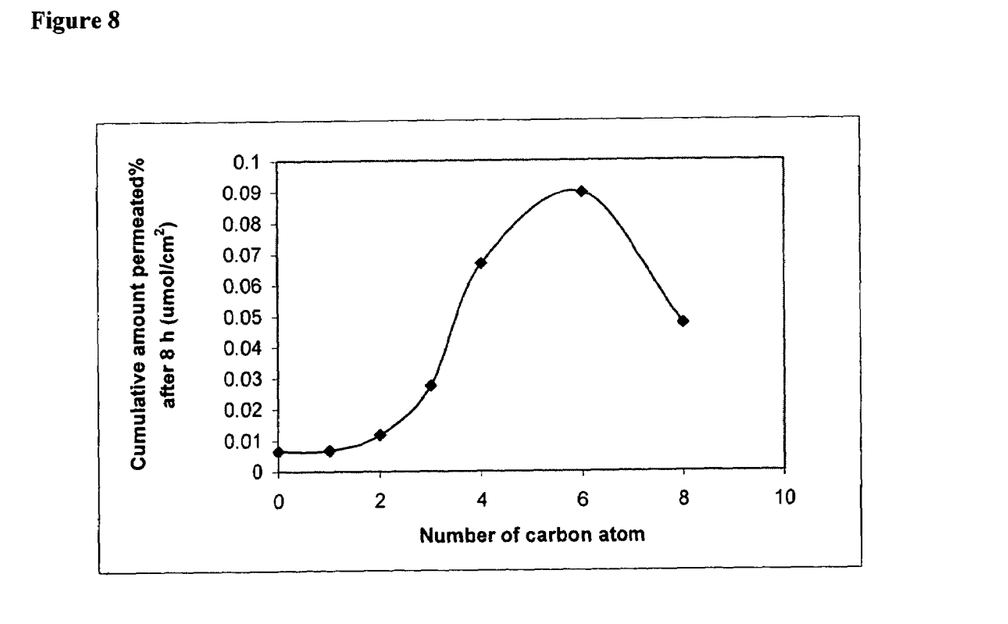
FIG. 8 depicts a correlation of cumulative amount permeated % of the temozolomide esters after 8 h across the full-thickness rat skin with the ester alkyl chain lengths.

FIG. 8 shows the accumulated concentrations of temozolomide methyl, ethyl, propyl, butyl, hexyl, octyl esters permeating through the whole rat skin over 8 hours. It is clear the alkyl group consisting of six carbons ($C_6$) renders the maximized permeation.

Figure 9:
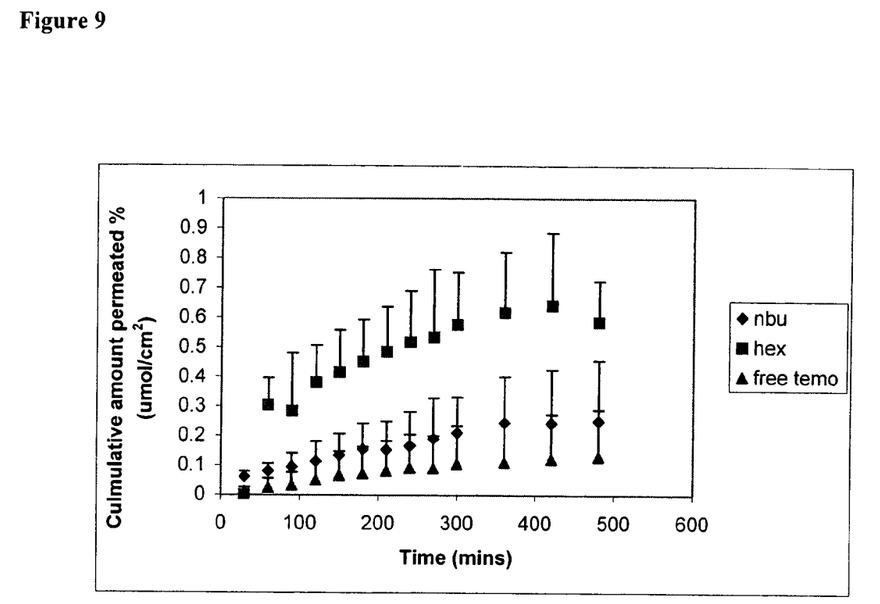
FIG. 9 depicts permeation of temozolomide, temozolomide n-hexyl ester, and temozolomide n-butyl amide through human skin.

Based on the results from the experiments with the synthetic silicon membrane and the whole rat skin, the temozolomide hexyl ester and the temozolomide n-butyl amide are chosen to perform permeation studies using human skins in comparison with the temozolomide. The results are depicted in FIG. 9. It is clear that the permeations of both the ester and the amide through human skins are notably better than temozolomide. This demonstrates the temozolomide ester pro-drug strategy is a feasible approach for treatment of cancers through topical and transdermal application. Same to the results from the rat skin, the hexyl ester is completely metabolized into the temozolomide acid by esterase enzymes within the human skin. Again, the n-butyl amide is resistant to metabolism by the enzymes in human skin.

The temozolomide hexyl ester is chosen to conduct an in viva antitumour test. BALB/c nude mice were inoculated with MV3 melanoma (human). Once the tumour volume became 100–300 mm$^3$, the mice were divided into a controlled and a tested group of eight with a rational distribution of the mice according to the sizes of the tumours. The tested group was treated with 5% (W/V) free made dimethyl sulfoxide (DMSO) solution of the temozolomide hexyl ester twice a day (once on Saturday and Sunday) via repeated topical application (total dosage is 20 mg/mouse/day), while the controlled group was left to grow naturally. In a period of two-week experiment, the tumour growth in the mice was carefully recorded through body weighing and the measurement of the tumour sizes. After two weeks, the mice were scarified; tumour bulks were separated and weighed. The results of inhibition of tumour growth by the temozolomide hexyl ester are summarized in Table 5 and depicted in FIG. 10.

TABLE 5

In Vivo inhibition activity of the temozolomide hexyl ester against MV3 Melanoma in Mice (20 mg/mouse/day)

| Group | No. of animals | | Body weight (g)[a] | | Tumour volume (mm³)[a] | | RTV | T/C (%) | Tumour weight (g)[a] | Inhibition (%) |
|---|---|---|---|---|---|---|---|---|---|---|
| | start | end | start | end | start | end | | | | |
| Controlled | 8 | 8 | 23.7 ± 1.50 | 25.0 ± 0.535 | 105 ± 79.9 | 2381 ± 980.3 | 8.92 ± 8.97 | | 2.10 ± 0.802 | |
| Tested | 8 | 8 | 24.0 ± 1.53 | 22.9 ± 2.23 | 116 ± 27 | 622 ± 545.1* | 3.01 ± 1.95 | 33.7 | 0.41 ± 0.318 | 80.5 |

*P < 0.05 vs control.
[a]Body weight (g), tumour volume (mm³) and tumour weight (g) were expressed by mean ± SD.

In the two week experiments by topical application of the temozolomide hexyl ester at the dosage of 20 mg per day, the growth inhibition rate of the temozolomide hexyl ester against MV3 melanoma (human) in the mice is 80.5% with T/C (%) 33.7. This result demonstrates the temozolomide esters are effective anticancer pro-drugs.

In conclusion, the above experiments with the synthetic silicon membrane, the whole rat skin and the human skin, demonstrate the temozolomide esters posse potent skin permeating ability and are readily metabolised into the bioactive temozolomide acid. The in vivo bioactivity test of the temozolomide hexyl ester with the BALB/c nude mice inoculated with MV3 melanoma proves the temozolomide ester are potent anticancer pro-drugs, particularly for topical and transdermal application.

The superior topical and transdermal applicable properties of the temozolomide esters do not deny their potential to be used in oral and injection forms in treatments of cancers.

The invention will now be further illustrated by reference to the following examples, but not restricted by the examples.

NMR (Nuclear Magnetic Resonance) data were collected on a Bruker NMR AC 250 spectrometer, IR (Infrared) data were measured on an IR MATTSON 3000 FTIR spectrometer, HPLC (high performance liquid chromatography) analysis was performed on a SHIMADZU SPD-10A vp system and MS (Mass Spectropic) data were collected on an HP G1034C MS chemstation spectrometer. The abbreviations of DMF, THF, DMAP, $d_6$-DMSO and $D_2O$ used in examples stand for dimethylformamide, tetrahydrofuran, 4-dimethylaminopyridine, deuterium dimethyl sulphoxide and deuterium oxide respectively. PyBrOP® (bromo-tri-pyrrolidino-phosphonium hexafluorophosphate) was bought from Calbiochem-Novabiochem Corp. UK.

EXAMPLE 1

Synthesis of 3,4-dihydro-3-methyl-4-oxoimidazo[5,1-d]-1,2,3,5-tetrazine-8-carboxylic acid (the temozolomide acid)

8-Carbamoyl-3-methylimidazo[5,1-d]-1,2,3,5-tetrazine-4 (3H)-one (temozolomide) (2.577 mmol, 0.5 g) was stirred in 4 ml of conc. $H_2SO_4$. To the mixture was dropwise added sodium nitrite (9.4 mmol, 0.65 g) in 2.6 ml water on an ice bath at temperatures below 15° C., and then the mixture was kept stirring for 16 hours at room temperature. Ice water (10 ml) was added into the reaction mixture and cooled on ice bath for 1 hour. The precipitated solid temozolomide acid was collected with filtration and dried under vacuum (0.493 g, 98.6% yield).

$^1$H NMR ($d_6$-DMSO/ppm) δ 8.82 (s, 1, H-6), 3.87 (s, 3, C$\underline{H}_3$—N) $^{13}$C NMR ($d_6$-DMSO/ppm) δ 162 ($\underline{C}OO$), 140 (C-4), 137 (C-6), 130 (C-9), 128 (C-8), 37 (N$\underline{C}H_3$).

EXAMPLE 2

The General Procedure for Synthesis of alkyl or S-alkyl 3,4-dihydro-3-methyl-4-oxoimidazo[5,1-d]-1,2,3,5-tetrazine-8-carboxylates or -carbothioates (temozolomide esters or temozolomide thiol esters)

Method A.

The temozolomide acid (1 mmol, 0.195 g), triethylamine (0.3 ml) and catalytic amount of iodine (about 2 mg) were mixed with dried DMF (2 ml). To the mixture was added an appropriate bromo-alkane (2 mmol) and the mixture was stirred for 4 hours at room temperature. Water (3 ml) was added and aqueous phase was separated. The remained mixture was concentrated under reduced pressure and the residue was purified by a silica gel flush column to give the target product. The esters were characterized by using IR, $^1$H-NMR and $^{13}$C-NMR spectroscopic, and mass spectrometry (MS) technology, and the data listed individually bellow.

Method B

Dried DMF (2 ml), and dried THF (3 ml) were added into a flask containing the temozolomide acid (1 mmol, 0.195 g) and Pybrop® (1 mmol, 0.466 g), and the mixture stirred until the solids were completely dissolved. In an ice bath, the appropriate dried alcohol or thiol (2.2 mmol) was added into the mixture followed by the addition of DMAP (2 mmol, 0.244 g). The reaction was allowed to continue for half an hour, then stirred at room temperature for 16 hours. The suspension was filtered through a Buchner funnel and the solvent was evaporated. Ice water (10 ml) was added to the residue and extracted with ethyl acetate (10 ml×3). The combined ethyl acetate layer was dried over magnesium sulphate. After the ethyl acetate was evaporated, the residue was purified on silica gel columns. The solvent was evaporated to give the ester products same to the above.

1. Methyl 3,4-dihydro-3-methyl-4-oxoimidazo[5,1-d]-1,2,3,5-tetrazine-8-carboxylate (temozolomide methyl ester)

$^1$H NMR ($d_6$-DMSO/ppm) δ 8.86 (s, 1, H-6), 3.90 (s, 3, C$\underline{H}_3$—O), 3.87 (s, 3, C$\underline{H}_3$—N) $^{13}$C NMR ($d_6$-DMSO/ppm) δ 161 ($\underline{C}OO$), 139 (C-4), 137 (C-6), 129 (C-9), 126 (C-8), 52.2 (O$\underline{C}H_3$), 36.4 (N$\underline{C}H_3$) $v_{max}$ (KBr): 3489, 2961 (C—H), 1752 (C=O), 1727 (C=O), 1214 (C—O), 1062 (C—O), 828, 556 cm$^{-1}$ MS: +ES: m/z=232 [M+Na]$^+$.

2. Ethyl 3,4-dihydro-3-methyl-4-oxoimidazo[5,1-d]-1,2,3,5-tetrazine-8-carboxylate (temozolomide ethyl ester)

$^1$H NMR (CDCl$_3$/ppm) δ 8.45 (s, 1, H-6), 4.52 (q, 2, J=7.1 Hz, C$\underline{H}_2$—O), 4.04 (s, 3, C$\underline{H}_3$—N), 1.45 (t, 3, J=7.1 Hz, CH$_2$—C$\underline{H}_3$) $^{13}$C NMR ($d_6$-DMSO/ppm) δ 161 ($\underline{C}OO$), 139 (C-4), 137 (C-6), 129 (C-9), 127 (C-8), 60.9 (O$\underline{C}H_2$), 36.4

(NCH₃), 14.3 (CH₂CH₃) ν$_{max}$ (KBr): 3478, 2991 (C—H), 1754 (C=O), 1700 (C=O), 1467 (C—O),1258 (C—O), 1060 (C—O), 844, 561 cm⁻¹

MS: +ES: m/z=246 [M+Na]⁺.

3. n-Propyl 3,4-dihydro-3-methyl-4-oxoimidazo[5,1-d]-1,2,3,5-tetrazine-8-carboxylate (temozolomide n-propyl ester)

¹H NMR (CDCl₃/ppm) δ 8.46 (s, 1, H-6), 4.41 (t, 2, J=6.7 Hz, CH₂—O), 4.03 (s, 3, CH₃—N), 1.83 (sextet, 2, J=7.1 Hz, C—CH₂—C), 1.03 (t, 3, J=7.4 Hz, C—CH₃) ¹³C NMR (CDCl₃/ppm) δ 160 (COO), 138 (C-4), 136 (C-6), 130 (C-9), 128 (C-8), 67.1 (OCH₂), 36.5 (NCH₃), 21.7 (CH₂CH₃), 8.87 (CH₂CH₃) ν$_{max}$ (KBr): 3122, 2960 (C—H), 1729 (C=O), 1700(C=O), 1457 (C—O), 1200 (C—O), 1174 (C—O), 1052, 942 cm⁻¹ MS: +ES: m/z=260 [M+Na]⁺.

4. n-Butyl 3,4-dihydro-3-methyl-4-oxoimidazo[5,1-d]-1,2,3,5-tetrazine-8-carboxylate (temozolomide n-butyl ester)

¹H NMR (CDCl₃/ppm) δ 8.45 (s, 1H-6), 4.45 (t, 2, J=7.1 Hz, CH₂—O), 4.03 (s, 3, CH₃—N), 1.79 (quintet, 2, J=7.4 Hz, C—CH₂—C), 1.46 (sextet, 2, J=7.3 Hz, C—CH₂—CH₃), 0.95 (t, 3, J=7.3 Hz, C—CH₃) ¹³C NMR ($_{d6}$-DMSO/ppm) δ 161 (COO), 139 (C-4), 137 (C-6), 129 (C-9), 127 (C-8), 64.5 (OCH₂), 36.4 (NCH₃), 30.3 (OCH₂CH₂), 18.7 (CH₂CH₃), 13.6 (CH₂CH₃) ν$_{max}$ (KBr): 3156, 2967 (C—H), 1746 (C=O), 1467 (C—O), 1261 (C—O), 1054 (C—O), 823, 561 cm⁻¹ MS:+ES: m/z=274 [M+Na]⁺.

5. S-n-Butyl 3,4-dihydro-3-methyl-4-oxoimidazo[5,1-d]-1,2,3,5-tetrazine-8-carbothioate (temozolomide S-n-butyl thiol ester)

¹H NMR (CDCl₃/ppm) δ 8.30 (s, 1 H-6), 3.89 (s, 3, CH₃—N),2.97 (t, 2, J=7.1 Hz, CH₂—S), 1.3 (quintet, 2, J=7.4 Hz, C—CH₂—C), 1.36 (sextet, 2, J=7.3 Hz, C—CH₂—CH₃), 0.96 (t, 3, J=7.3 Hz, C—CH₃) ¹³C NMR ($_{d6}$-DMSO/ppm) δ 191.8 (COS), 143 (C-4), 139 (C-6), 137 (C-9), 133 (C-8), 36.7 (NCH₃), 33.5 (SCH₂), 30.5 (SCH₂CH₂), 20.9 (CH₂CH₃), 13.8 (CH₂CH₃) ν$_{max}$ (KBr): 3156, 2967 (C—H), 1696 (C=S)cm⁻¹ MS:+ES: m/z=290 [M+Na]⁺.

6. n-Pentyl 3,4-dihydro-3-methyl-4-oxoimidazo[5,1-d]-1,2,3,5-tetrazine-8-carboxylate (temozolomide pentyl ester)

¹H NMR (CDCl₃/ppm) δ 8.46 (s, 1, H-6), 4.45 (t, 2, J=7.0 Hz, CH₂—O), 4.03 (s, 3, CH₃—N), 1.79 (quintet, 2, J=7.1 Hz, C—CH₂—C), 1.29–1.40 (m, 4, C—(CH₂)₂—C), 0.96 (t, 3, J=6.9 Hz, C—CH₃) ¹³CMR ($_{d6}$-DMSO/ppm) δ 161 (COO), 139 (C-4), 137 (C-6), 129 (C-9), 127 (C-8), 64.6 (OCH₂), 36.4 (NCH₃), 30.9 (OCH₂CH₂), 28.2 (O(CH₂)₂CH₂), 22.8 (CH₂CH₃), 14.0 (CH₂CH₃) ν$_{max}$ (KBr): 3136, 2967 (C—H), 1736 (C=O), 1459 (C—O), 1231 (C—O), 1154 (C—O), 923, 761 cm⁻¹ MS:+ES: m/z=288 [M+Na]⁺.

7. S-n-Pentyl 3,4-dihydro-3-methyl-4-oxoimidazo[5,1-d]-1,2,3,5-tetrazine-8-carbothioate (temozolomide S-n-pentyl thiol ester)

¹H NMR (CDCl₃/ppm) δ 8.34 (s, 1, H-6), 4.01 (s, 3, CH₃—N),3.12 (t, 2, J=7.0 Hz, CH₂—S), 1.89 (quintet, 2, J=7.1 Hz, C—CH₂—C), 1.29–1.33 (m, 4, C—(CH₂)₂—CH₃), 0.94 (t, 3, J=6.9 Hz, C—CH₃) ¹³CMR ($_{d6}$-DMSO/ppm) δ 190 (COS), 142 (C-6), 139 (C-4),137(C-8), 135 (C-9), 36.4 (NCH₃), 34.6 (SCH₂), 31.2 (S(CH₂)₂CH₂), 28.4 (SCH₂CH₂), 22.5 (CH₂CH₃), 14.1 (CH₂CH₃) ν$_{max}$ (KBr): 3136, 2967 (C—H), 1700 (C=S) cm⁻¹ MS:+ES: m/z=304 [M+Na]⁺.

8. Hexyl 3,4-dihydro-3-methyl-4-oxoimidazo[5,1-d]-1,2,3,5-tetrazine-8-carboxylate (temozolomide hexyl ester)

¹H NMR (CDCl₃/ppm) δ 8.49 (s, 1, H-6), 4.45 (t, 2, J=6.9 Hz, CH₂—O), 4.04 (s, 3, CH₃—N), 1.79 (quintet, 2, J=7.1 Hz, C—CH₂—C), 1.29–1.40 (m, 6, C—(CH₂)₃—CH₃), 0.87 (t, 3, J=6.9 Hz, C—CH₃) ¹³CMR ($_{d6}$-DMSO/ppm) δ 161 (COO), 139 (C-4), 137 (C-6), 129 (C-9), 127 (C-8), 64.8 (OCH₂), 36 (NCH₃), 30 (OCH₂CH₂), 28 (O(CH₂)₂CH₂), 25.1 (CH₂CH₂CH₃), 22.1 (CH₂CH₃), 13.9 (CH₂CH₃) ν$_{max}$ (KBr): 3156, 2967 (C—H), 1746 (C=O), 1467 (C—O), 1261 (C—O), 1054 (C—O), 823, 561 cm⁻¹ MS:+ES: m/z=302 [M+Na]⁺.

9. S-n-Hexyl 3,4-dihydro-3-methyl-4-oxoimidazo[5,1-d]-1,2,3,5-tetrazine-8-carbothioate (temozolomide S-n-hexyl thiol ester)

¹H NMR (CDCl₃/ppm) δ 8.31 (s, 1, H-6), 4.02 (s, 3, CH₃—N),3.00 (t, 2, J=6.9 Hz, CH₂—S), 1.96 (quintet, 2, J=7.1 Hz, C—CH₂—C), 1.29–1.38 (m, 6, C—(CH₂)₃—CH₃), 0.91 (t, 3, J=6.9 Hz, C—CH₃) ¹³CMR ($_{d6}$-DMSO/ppm) δ 191.7 (COS), 141.3 (C-6), 139.0 (C-4), 137.1 (C-8), 131.2 (C-9), 36.4 (NCH₃), 34.8 (SCH₂), 30.9 (SCH₂CH₂), 29.2 (S(CH₂)₂CH₂), 28.1 (CH₂CH₂CH₃), 22.4 (CH₂CH₃), 14.0 (CH₂CH₃) ν$_{max}$ (KBr): 3156, 2967 (C—H), 1686 (C=S) cm⁻¹ MS:+ES: m/z=318 [M+Na]⁺.

10. n-Heptyl 3,4-dihydro-3-methyl-4-oxoimidazo[5,1-d]-1,2,3,5-tetrazine-8-carboxylate (temozolomide n-heptxyl ester)

¹H NMR (CDCl₃/ppm) δ 8.39 (s, 1, H-6), 4.38 (t, 2, CH₂—O), 4.00 (s, 3, CH₃—N), 1.75 (s, 2, C—CH₃—C), 1.19 (s, 8, C—(CH₂)₄—C), 0.83 (s, 3, C—CH₃) ¹³C NMR ($_{d6}$-DMSO/ppm) δ 161 (COO), 139 (C-4), 137 (C-6), 129 (C-9), 127 (C-8), 64.8 (OCH₂), 36.4 (NCH₃), 31.1 (OCH₂CH₂), 2×28.4 (OCH₂CH₂(CH₂)₂), 25.3 (CH₂CH₂CH₃), 22.1 (CH₂CH₃), 13.8 (CH₂CH₃) ν$_{max}$ (KBr): 3146, 2927 (C—H), 2858 (C—H), 1748 (C=O), 1718 (C=O), 1457 (C—O), 1245 (C—O), 828, 566 cm⁻¹ MS:+ES: m/z=316 [M+Na]⁺.

11. n-Octyl 3,4-dihydro-3-methyl-4-oxoimidazo[5,1-d]-1,2,3,5-tetrazine-8-carboxylate (temozolomide n-octyl ester)

¹H NMR (CDCl₃/ppm) δ 8.36 (s, 1, H-6), 4.36 (s, 2, CH₂—O), 3.95 (s, 3, CH₃—N), 1.74 (s, 2, C—CH₃—C), 1.19 (s, 10, C—(CH₂)₅—C), 0.78 (s, 3, C—CH₃) ¹³C NMR ($_{d6}$-DMSO/ppm) δ 160 (COO), 139 (C-4), 137 (C-6), 129 (C-9), 127 (C-8), 64.8 (OCH₂), 36.4 (NCH₃), 31.2 (OCH₂CH₂), 2×28.6 (OCH₂CH₂(CH₂)₂), 28.2 (O(CH₂)₄CH₂), 25.4 (CH₂CH₂CH₃), 22.1 (CH₂CH₃), 13.9 (CH₂CH₃) ν$_{max}$ (KBr): 2925, 2853, 1758, 1720, 1467, 1255, 838, 556 cm⁻¹ MS:+ES: m/z=330 [M+Na]⁺.

EXAMPLE 3

Synthesis of 3-methyl-N-(iso-propyl, n-butyl, iso-butyl or ter-butyl)-4-oxoimidazo[5,1-d]-1,2,3,5-tetrazine-8-carboxamides (temozolomide amide derivatives)

Temozolomide amide derivatives were prepared using the Method B of EXAMPLE 2 for temozolomide esters, except 1.1 mmol of the dried alkylamine was used instead of the dried alcohol. The amides were characterized by using IR, ¹H-NMR and ¹³C-NMR spectroscopic, and mass spectrometry (MS) technology and microanalysis, and the data listed individually bellow.

12. 3-Methyl-N-(iso-propyl)-4-oxoimidazo[5,1-d]-1,2,3,5-tetrazine-8-carboxamide (temozolomide iso-propyl amide)

¹H NMR ($_{d6}$-DMSO/ppm) δ 8.83 (s, 1, H-6), 8.21 (d, 1, J=8.4 Hz, C—NH—C), 4.13 (sextet, 1, J=6.9 Hz, N—

CH—(CH$_3$)$_2$, 3.85 (s, 3, CH$_3$—N), 1.19 (s, 3, CH$_3$—CH), 1.17 (s, 3, CH$_3$—CH $^{13}$C NMR ($_{d6}$-DMSO/ppm) δ 159 (CONH), 139 (C-4), 134 (C-6), 131 (C-9), 128 (C-8), 36.2 (NCH$_3$), 22.2 (CH(CH$_3$)$_2$) $v_{max}$ (KBr): 3436 (N—H), 2973 (C—H), 2336, 1758 (C=O), 1652 (C=O), 1471 (C—N), 1263 (C—N), 832, 561 cm$^{-1}$ MS:+ES: m/z=259 [M+Na]$^+$.

13. 3-Methyl-N-(n-butyl)-4-oxoimidazo[5,1-d]-1,2,3,5-tetrazine-8-carboxamide (temozolomide n-butyl amide)

$^1$H NMR (CDCl$_3$/ppm) δ 8.38 (s, 1, H-6), 7.35 (m, 1, C—NH—C), 3.99 (s, 3, CH$_3$—N), 3.48 (q, 2, J=6.7 Hz, N—CH$_2$—C), 1.60 (quintet, 2, J=7.3 Hz, C—CH$_2$—C), 1.39 (sextet, 2, J=7.3 Hz, C—CH$_2$—CH$_3$), 0.93 (t, 3, J=7.3 Hz, C—CH$_3$) $^{13}$C NMR ($_{d6}$-DMSO/ppm) δ 160 (CONH), 139 (C-4), 134 (C-6), 130 (C-9), 128 (C-8), 38.2 (NHCH$_2$), 36.2 (NCH$_3$), 31.4 (CH$_2$CH$_2$CH$_3$), 19.6 (CH$_2$CH$_3$), 13.7 (CH$_2$CH$_3$) $v_{max}$ (KBr): 3350 (N—H), 2957 (C—H), 2358, 1744 (C=O), 1654 (C=O), 1459 (C—N), 1251 (C—N), 842 cm$^{-1}$ MS:+ES: m/z=273 [M+Na]$^+$.

14. 3-Methyl-N-(iso-butyl)-4-oxoimidazo[5,1-d]-1,2,3,5-tetrazine-8-carboxamide (temozolomide iso-butyl amide)

$^1$H NMR (CDCl$_3$/ppm) δ 8.35 (s, 1, H-6), 7.46 (m, 1, C—NH—C), 3.99 (s, 3, CH$_3$—N), 3.35 (t, 2, J=7.1 Hz, NH—CH$_2$—CH), 1.92 (m, 1, C—CH—(CH$_3$)$_2$), 0.95 (s, 3, C—CH$_3$), 0.90 (s, 3, C—CH$_3$) (see appendix 17) $^{13}$C NMR ($_{d6}$-DMSO/ppm) δ 160 (CONH), 139 (C-4), 134 (C-6), 130 (C-9), 128 (C-8), 45.7 (NHCH$_2$), 35.9 (NCH$_3$), 27.9 (CH$_2$CH), 19.8 (CH(CH$_3$)$_2$) (see appendix 18) $v_{max}$ (KBr): 3400 (N—H), 2964 (C—H), 1762 (C=O), 1664 (C=O), 1600, 1500 (C—N), 1257 (C—N), 850, 550 cm$^{-1}$ MS:+ES: m/z=273 [M+Na]$^+$.

15. 3-Methyl-N-(tert-butyl)-4-oxoimidazo[5,1-d]-1,2,3,5-tetrazine-8-carboxamide (temozolomide tert-butyl amide)

$^1$H NMR (CDCl$_3$/ppm) δ 8.39 (s, 1, H-6), 4.08 (s, 3, CH$_3$—N), 1.42 (s, 9, C—(CH$_3$)$_3$) $^{13}$C NMR ($_{d6}$-DMSO/ppm) δ 159 (CONH), 139 (C-4), 134 (C-6), 130 (C-9), 128 (C-8), 50.8 (C(CH$_3$)$_3$), 36.2 (NCH$_3$), 28.5 (C(CH$_3$)$_3$) $v_{max}$ (KBr): 3389 (N—H), 2963 (C—H), 1764 (C=O), 1664 (C=O), 1587 (C—N), 1471 (C—N), 838, 561 cm$^{-1}$ MS:+ES: m/z=273 [M+Na]$^+$.

EXAMPLE 4

Enzymatic Metabolizing Studies of methyl 3,4-dihydro-3-methyl-4-oxoimidazo[5,1-d]-1,2,3,5-tetrazine-8-carboxylate (the temozolomide methyl ester)

Enzymatic metabolizing studies of the temozolomide methyl ester was carried out using pig liver esterase enzyme from Sigma [a suspension in 3.2 M ammonium sulphate solution pH 8; 200 unit/mg protein (14 mg protein/ml)].

A. To a NMR tube 2 mg of the temozolomide methyl ester was added, followed by 0.2 ml of $_{d6}$-DMSO, 0.5 ml D$_2$O of pH 7.4 sulphate buffer and finally 50 μl of the enzyme solution. Record a $^1$H NMR spectrum immediately, then the mixture was incubated at 37° C. and record a $^1$H NMR spectrum at each 5 minutes time interval. The results are showed in FIG. 1.

B. In the same manner, the temozolomide n-butyl amide was studied. The samples were dissolved in $_{d6}$-DMSO in an NMR tube, 50 μl of enzyme solution was added and the solution incubated at 37° C. The samples were periodically subjected to analysis by $^1$H-NMR for up to 8 hours and no the temozolomide acid was observed.

EXAMPLE 5

Studies of the Solubility of Temozolomide and the Temozolomide Esters

The solubility of temozolomide and the temozolomide esters was determined in 10% v/v propylene glycol by stirring an excess of the solid products at room temperature for 5 hours. The mixtures were then filtered, diluted with sample solvent and analysed using HPLC. No breakdown products were detected in the period of experiments and the results were summarized in Table 1.

EXAMPLE 6

In Vitro Permeation Studies

Materials and Equipments

Figure 2:
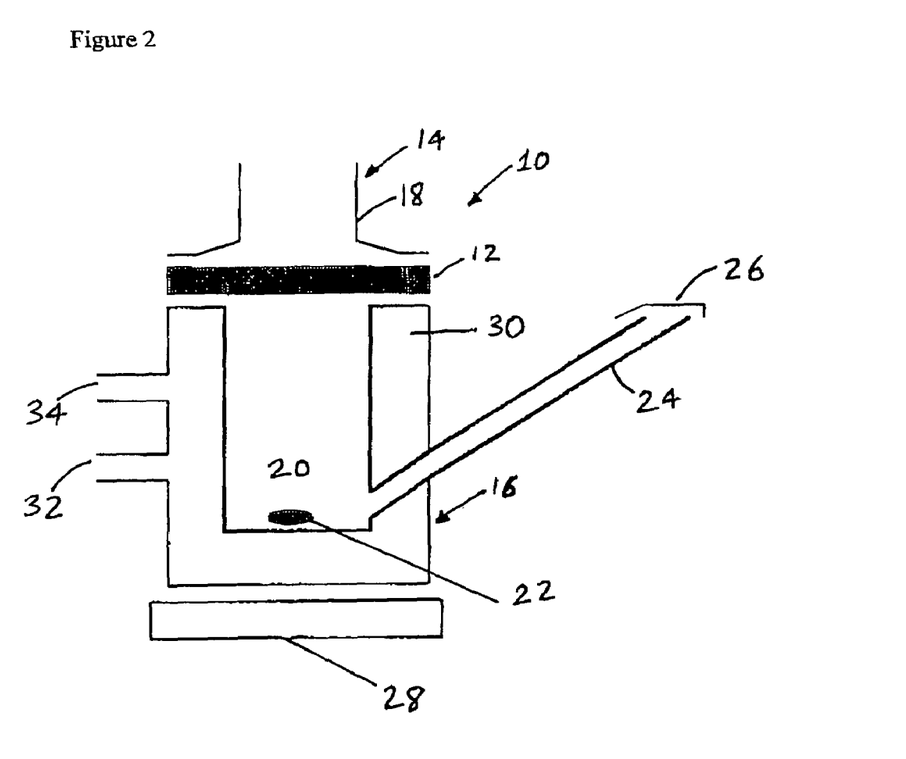
FIG. 2 schematically illustrates a diffusion cell for transdermal experiments.

Jacketed Franz-type diffusion cells were used throughout the study and the barrier (12) (skin or silicone membrane) was mounted between the two chambers (14, 16) (2.8–3.4 cm$^2$ available surface area) with the dermal side in contact with the receiver solution (FIG. 2). The diffusion chambers (10) comprised a barrier of skin or silicone membrane (12) mounted between two chambers (14, 16). A cap (18) formed the donor compartment (14). The second receptor compartment (16) contained a receptor cell (20) with a stirring bar (22), sampling port (24) and cover (26). The stirring bar (22) was stirred by means of a magnet plate (28) having a rotating magnet. The receptor compartment comprised a water jacket (30) having a water inlet (32) and a water outlet (34).

Double distilled water was boiled to get rid of the air bubbles and then it was allowed to cool down to room temperature. Finally, it was sonicated to completely de-gas.

Three types of materials were used in permeation studies.

1. Silicone membrane (Silastic Medical Grade, 500-5, Dow Corning 0.005 in thick) was cut into circular sections (2 cm diameter) and washed with double distilled water prior to use.
2. Full-thickness rat skin was obtained from Male Wistar rats aged 10 to 12 weeks and weighing 250 to 300 g, which were sacrificed by cervical dislocation, the abdomen shaved and the intact skin removed by dissection. Following removal of fat tissue, the skin was cut into circular pieces and used immediately.
3. Samples of adult human epidermis were purchased from the Stephen Kirby Skin Bank (UK). The samples were from the leg of a Caucasian male, were stored at −18° C. and used within one week.

Experiments

The membrane (as detailed above) was mounted on the diffusion cell (10), on which the surface area available for diffusion of each cell was about 2.8–3.4 cm$^2$. The cell cap (18) was placed on the membrane (12), and it was sealed with Parafilm® connecting the cell cap, membrane, and receptor cell. The capacity of each receptor cell was around 25–26 ml, which was filled with receptor solution and was completely in contact with the membrane sheet. During the course of experiment, the solution was continuously stirred by teflon-coated magnetic bar (22) placed in the cell (20). The temperature was maintained at 37° C. by a thermostatic water pump that circulated the water through the jacket (30) surrounding the cell body. The system was allowed to equilibrate under these conditions for half an hour. Finally, the prepared sample solution (2 ml) was added into the donor cap cell, and it was sealed with Parafilm® to minimize the evaporation of donor solution. 1 ml of receptor solution was removed every 30 minutes for 5 hours and then every 60 minutes for a further 3 hours. The volumes withdrawn were always replaced with equal volumes of fresh receptor solution to maintain constant volume. The concentration of each sample solution was determined by using HPLC.

For every sample, six determinations were performed on human and rat skin, and three determinations were carried out through artificial silicone membrane. The mean values were used for correlation and comparisons and the results were showed in FIGS. 3 to 9.

As stated above, after the removal of receptor solution, the receiver compartment was refilled with an identical volume of receptor fluid. This causes of the dilution of receptor solution leading to an under determination of the sample concentration. As a consequence, it was necessary to mathematically correct each successive sample concentrations, in the present invention, which was determined by applying the following equation:

$$C_t = C_{mt} + \left[ V_s \cdot \frac{\sum_{t=1}^{t=n-1} C_m}{V_r} \right]$$

where $C_t$ is the actual current concentration of drug in the receptor phase at time t, $C_{mt}$ is the apparent (i.e. measured) current concentration of drug in the receptor phase, $V_s$ is the sample volume withdrawn for analysis, $V_r$ is the volume of receptor solution, and $\Sigma C_m$ is the summed total of the previous measured concentrations.

Finally, the amount of drug penetrating the skin per unit area was calculated by dividing the obtained concentrations by the surface area available for diffusion cell and this value was different for each individual cell. In the present invention, the results were expressed in term of % cumulative amount permeated (μg for permeation test through silicone membrane, and μmol for rat and human skin) per square centimetre of surface area of diffusion cell ($cm^2$) (Bodor and Sloan, 1983).

EXAMPLE 7

In Vitro Tumour Cell Growth Inhibition Tests

Temozolomide (white powder), temozolomide acid (white powder) and temozolomide-8-carboxylate hexyl (white scale crystal) were made in house. For the estimation of in vitro tumour cell growth inhibition, MV3 (human melanoma), M14 (human melanoma), B16 and B16-BL6 (mouse melanoma), SHG-44, TJ899 and TJ905 (human glioma), MCF-7 (human breast), HCT-8 (human colon), A549 (human non small lung), Bel7402 (human hepatocellulor), and BGC-823 (human stomach) were used. All tumour cells were cultured in RPMI-1640 medium supplemented with 10% fetal bovine serum (FBS) at 37° C. in a humidified 5% $CO_2$ incubator.

Experiment:

After being harvested from culture flasks, a cell suspension of $1\times10^4$/ml was made by using 1640 RPMI medium supplemented with 10% fetal bovine serum. 100 μl (contains 1000 tumour cells) of the cell suspension was seeded per well of 96-well flat-bottom Costar culture plates at 37° C. in a humidified 5% $CO_2$ incubator for 24 hrs before introducing drugs. Each tested compounds was made for five different concentrations and 100 μl of the each concentration was introduced into parallel three wells; control wells were added with 100 μl of plain medium alone; fluorouracil (a chemotherapeutic antitumour drug) was used as the positive control. Cells were then incubated for 96 h. Proliferative response and cell death were determined using MTT (3-(4, 5-dimethylthiazolyl)-2,5-diphenyl-tetrazolium bromide) assay.

MTT assay: Following incubation of cells with the tested compounds for 96 h, 100 μl of 0.4 mg/ml MTT in RPMI 1640 was added to each well and the plate was incubated at 37° C. for 4 h. The plate was then centrifuged and followed by removal of medium. 150 μl of DMSO was then added to dissolve formazan crystal. DMSO-added plates were placed on a plate shaker for 5 min and absorbance was measured spectrophotometrically at 540 nm (with reference wavelength at 450 nm) using a Benchmark microtiter plate reader (Bio-Rad 550, Bio-Rad Laboratories, CA, U.S.A.).

The $IC_{50}$ was calculated from the curve of the tested compound concentrations against the inhibition rate of the tumour cells. Table 1 summarized the experiment results by using six human cancer cell lines, HCT-8 (colon carcinoma), A549 (non small lung carcinoma), MCF-7 (breast), Bel7402 (hepatocellulor carcinoma), BGC-823 (stomach adenocarcinoma), and MV3 (melanoma). Table 2 summarized the results from the experiment results by using two human melanoma cell lines, MV3 and M14, two mouse melanoma cell lines, B16 and B16-BL6, and three human glioma cell lines, TJ899, SHG-44 and TJ905.

EXAMPLE 8

In Vivo Antitumour Activity Test of the Temozolomide Hexyl Ester on BALB/c Nude Mice Inoculated with MV3 Melanoma Preparation of 5% (W/V) DMSO solution of the temozolomide hexyl ester is carried out by weighing a actual amount of the temozolomide hexyl ester, then using DMSO to make the concentration to 50 mg/ml. After temozolomide hexyl ester is completely dissolved and a clear solution is obtained, the fresh made 5% (W/V) DMSO solution of the temozolomide hexyl ester is used in the experiments.

BALB/c nude mice were inoculated with MV3 melanoma (human). Once the tumour bulk became 100–300 $mm^3$, the mice were divided into a controlled and a tested group with a rational distribution of the mice according to the sizes of the tumours. Each group is consisted of 8 mice.

The tested group was treated with 5% (W/V) DMSO solution of the temozolomide hexyl ester twice a day (once on Saturday and Sunday) via repeated topical application on position of tumour and around of 2×2 $cm^2$ region (total dosage is 20 mg/mouse/day); while the controlled group was left free of treatment to allow the tumour to growth naturally.

Figure 10:
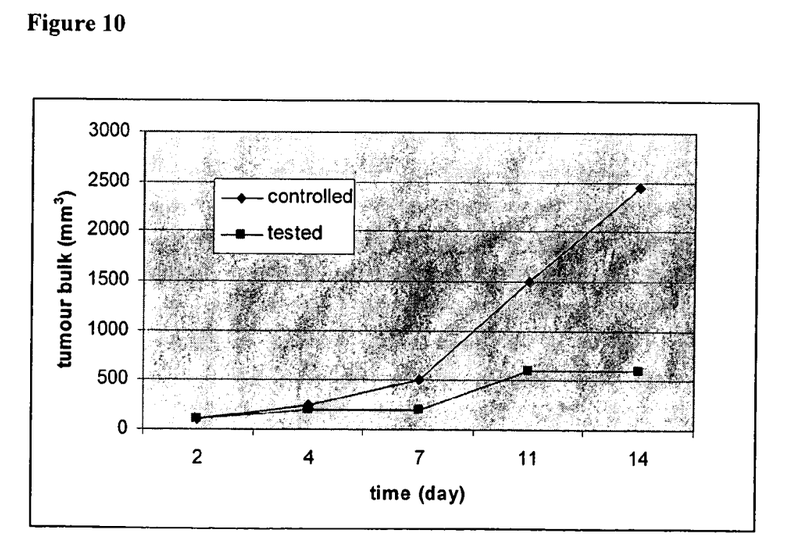
FIG. 10 depicts inhibition of tumour growth by temozolomide hexyl ester in mice inoculated with MV3 melanoma (human).

The tumour volumes (TV) in the mice were measured for twice of a week, calculated using TV($mm^3$)=(length× $width^2$)÷2, and carefully recorded and finally depicted in FIG. 10. After two weeks, the mice were scarified; tumour bulks were isolated, weighed and calculated the growth inhibition rate of MV3 melanoma (human) in BALB/c nude mice by the temozolomide hexyl ester. The antitumour activity of the temozolomide hexyl ester against MV3 melanoma (human) in BALB/c nude mice is evaluated by the relative tumour proliferation ratio (T/C %). T/C (%) is calculated by the following equation:

$$T/C(\%) = \frac{RTV \text{ (Tested group)}}{RTV \text{ (Controlled group)}} \times 100$$

Where, RTV=Vt/Vo (Vo is the tumour volume (TV) at the time when the mice were divided into the tested group and the controlled group; Vt is the tumour volume (TV) were measured at each time interval FIG. 10). The criteria for effectiveness are (1) when T/C (%)>60, the compound is no effect; (2) when T/C (%)≦60 and statistically significant P<0.05, the compound is effect. In the case of the temozolomide hexyl ester, the T/C (%) in BALB/c nude mice bearing MV3 melanoma (human) is 33.7% (Table 3) and P<0.05.

REFERENCES

H. D. BeaU, K. B. Sloan, 2002. Topical delivery of 5-fluorouracil (5-FU) by 1,3-bisalkylcarbonyl-5-FU prodrugs, Int. J. Pharrn, 231, 43–49.

Bleehen N M, Newlands E S, Lee S M, Thatcher N, Selby P, Calvert A H, Rustin G J S, Brampton M, Stevens M F G. 1995. Cancer research campaign phase II trial oftemozolomide in metastatic melanoma. J Clin Oncol 13: 910–913.

Bodor N., Sloan K. B., 1983. Improved delivery through membranes XII: the effect of the incorporation of biphasic solubilizing groups into prodrugs of steroids. Int. J. Pharrn., 15, 235–250.

Bronaugh R. L., Maibach H. I, 1987. In vitro percutaneous absorption, in Dermatotoxicology 3rd ed. Marzulli F. N., and Maibach (Eds.), Hemisphere, New York, Washington, Philadelphia, London, 121–133.

Chien Y. W., 1992. Transdermal drug delivery and delivery systems, in Novel drug delivery systems, Chien Y. W. (Ed.), Marcel Dekker, New York, Basel, Hong Kong, 301–380.

Diez-Sales O., Perez-Sayas E., Martin-Villodre A., Herraez-Dominguez M., 1993. The prediction of percutaneous absorption: Influence of the dermis on in vitro permeation models. International Journal of Pharmaceutics, 100: 1–7.

Gajewski T F. 2004. Temozolomide for melanoma: new toxicities and new opportunities. J Clin Oncol 22: 580–581.

Heimberger A M, Archer G E, McLendon R E, Hulette C, Friedman A H, Friedman H S, Bigner D D, Sampson J H. 2000. Temozolomide delivered by intracerebral microinfusion is safe and efficacious against malignant gliomas in rats. Clin Can Res 6: 4148–4153

Higuchi W. I., Yu C-D., 1987, Prodrugs in transdermal delivery, in Transdermal delivery of drugs volume 111, Kydonieus A. F., and Berner B. (Eds.), CRC Press, Boca Raton, Fla., 44–83.

Hotchkiss, S. A. M., 1988. Dermal metabolism, in Dermal absorption and toxicity assessment, Roberts M. S., and Walters K. A. (Eds.), Marcel Dekker, New York, Basel, Hong Kong, 43–101.

Hotchkiss S. A. M. 1992. Skin as a xenobiotic metabolising organ, in Progress in drug metabolism, Gibson G. G. (Ed.), Taylor & Francis, London, Washington D.C., 217–262.

Kampffineyer H. G. 1989. Absorption and ester cleavage of methyl salicylate by skin of single-pass perfused rabbit ears. Xenobiotica, 19, 131–141.

Lopez A., Faus V., Diez-Sales O., Herraez M., 1998. Skin permeation model of phenyl alcohols: comparison of experimental conditions. International journal of pharmaceutics, 173, 183–191.

Loudon G. M., 1995. Constitutional isomers and nomenclature, in Organic chemistry 3rd ed., Loudon G. M. (Ed.), Benjamin/Cumming, Calif., 55–56

Maenpaa J., Dooley T., Wurz G., Vandeberg J., Robinson E., Emshoff V., Sipila P., Wiebe V., Day C., Degregorio M., 1993. Topical toremifene-A new approach for cutaneous melanoma. Cancer Chemother. Pharmacol., 32, 392–395.

Middleton M R, Grob J J, Aaronson N, Fierlbeck G, Tilgen W, Seiter S, Gore M, Aamdal S, Cebon J, Coates A, Dreno B, Henz M, Schadendorf D, Kapp A, Weiss J, Fraass D, Statkevich P, Muller M, Thatcher N. 2000. Randomised phase III study of temozolomide versus dacarbazine in the treatment of patients with advanced metastatic malignant melanoma. J Clin Oncol 18: 158–166.

Mossman T., 1983. Rapid calorimetric assay for cellular growth and survival: application to proliferation and cytotoxicity assays, J Immunol Methods 65: 55–63.

Rathbone D L, Su D, Wang Y and Billington D C. 1999. Soluble prodrugs of the anticancer drugs temozolomide and mitozolomide. J Pharm Pharmacol 51 (supplement): 26

Raymond E, Izbicka E, Soda H, Gerson S L, Dugan M, Von Hoff D D. 1997. Activity of temozolomide against human tumour colony-forming units. Clin Cancer Res., 3: 1769–1774.

Sampson J H, Archer G E, Villavicencio A T, McLendon R E, Friedman A H, Bishop W R, Bigner D D, Friedman H S. 1999. Treatment of neoplastic meningitis with intrathecal temozolomide. Clin Can Res., 5: 1183–1188.

Soe L., Wurz G. T., Maenpaa J. u., Hubbard G. B., Cadman T. B., Wiebe V. J., Theon A. P., deGregorio M. W., 1997. Tissue distribution of transdermal toremifene. Cancer Chemother. Pharmacol., 39, 513 520.

Stevens M G F, Hickman J A, Stone R, Gibson N W, Baig G, Lunt E, Newton C. 1984. Antitumour Imidazotetrazines. 1. Synthesis and chemistry of 8-carbamoyl-3-(2-chloroethyl)imidazo[5, I-d]tetrazin-4(3H)-one, a novel broad-spectrum anticancer agent. J. Med. Chem. 27, 196–201.

Stevens M G F, Hickman J A, Langman S P, Chubb D, Vickers L, Stone R, Baig G, Goddard C, Gibson N W, Slack J A, Newton C, Lunt E, Fizames C, Lavelle F. 1987. Antitumour activity and pharmacokinetics in mice of 8-carmaboyl-3-methyl-imidazo[5,1 d]-1,2,3,5-tetrazin-4(3H)-one (CCRG 81045; M&B 39831), a novel drug with potential as an alternative to dacarbazine. Cancer Res., 47: 5846–5852.

Su Y B, Sohn S, Krown S E, Livingston P O, Wolchok J D, Quinn C, Williams L, Foster T, Sepkowitz K A, Chapman P B. 2004. Selective CD4+Lymphopenia in melanoma patients treated with temozolomide: a toxicity with therapeutic implications. J Clin Oncol., 22: 610–616.

Tsang L L H, Quarterman C P, Gescher A, Slack J A. 1991. Comparison of cytotoxicity in vitro of temozolomide and dacarbazine, prodrugs of 3-methyl-(triazen-1-yl)imidazole-4-carboxamide. Cancer Chemother Pharmacol., 27: 342–346.

Tsang L L H, Fanner P B, Gescher A, Slack J A. 1990. Characterisation of urinary metabolites of temozolomide in humans and mice and evaluation of their cytotoxicity, Cancer Chemother Pharmacol 27: 429–436.

Valia K. H., Tojo K, Chien Y. W., 1985. Long-tern permeation kinetics of estradiol: (III) kinetic analyses of the simultaneous skin permeation and bioconversion of estradiol esters. Drug Dev. Ind. Pharm. 11, 1133–1173.

Wang Y, Stevens M F G. 1997. New synthetic routes to the antitumour drug temozolomide. J Org Chem., 62: 7288–7194.

What is claimed is:

1. A compound of formula (I)

(I)

in which
 X represents oxygen (O) or sulphur (S);
 R represents a $C_5$–$C_{10}$ alkyl, cycloalkyl, alkenyl or alkynyl group, each of the groups being optionally substituted by one or more substituent groups independently selected from halogen atoms, —$OR_1$, —$SR_1$, —$NR_1R_2$, and an optionally substituted phenyl group; and
 $R_1$ and $R_2$ each independently represent a hydrogen atom, or a $C_1$–$C_{10}$ alkyl, cycloalkyl, alkenyl or alkynyl group.

2. A compound according to claim 1, wherein R represents a $C_5$–$C_{10}$ alkyl, cycloalkyl, alkenyl or alkynyl group selected from n-pentyl, n-hexyl, n-heptyl, n-octyl, iso-pentyl, iso-hexyl, iso-heptyl, iso-octyl, cyclopentyl, cyclohexyl, cycloheptyl, cyclooctyl, pentenyl, hexenyl, heptenyl, octenyl, pentynyl, hexynyl, heptynyl, and octynyl.

3. A compound according to claim 1, wherein R represents a $C_5$–$C_{10}$ alkyl, cycloalkyl, alkenyl or alkynyl group selected further from n-pentyl, n-hexyl, n-heptyl, iso-pentyl, iso-hexyl, iso-heptyl, cyclopentyl, cyclohexyl, cycloheptyl, pentenyl, hexenyl and heptenyl.

4. A method of preparing a compound of formula (I) as defined in claim 1 and wherein X=O, comprising the step of directly esterifying temozolomide acid (formula II, 3,4-dihydro-3-methyl-4-oxoimidazo[5,1-d]-1,2,3,5-tetrazine-8-carboxylic acid) with a $C_5$–$C_{10}$ halo-alkyl compound in presence of a base.

(II)

5. Method according to claim 4, wherein the $C_5$–$C_{10}$ halo alkyl compound comprises a chloro, bromo or iodo alkane and the base is an organic base or an inorganic base selected from the group consisting of LDA, K-HMDS, LiTMP, triethylamine, diethylamine, Hünig's Base, urea, guanidine, aniline, diphenylamine, p-dimetylaminoaniline, 2,6-dimethylpyridine, DMAP, proton sponge, aziridine, indoles, imidazole, morphines, pyridines, pyrroles, pyrazines, pyrazoles, tetrahydropyrroles, DABCO, DBN, and DBU.

6. A method of preparing a compound of formula (I) as defined in claim 1 and wherein X=O or S comprising the step of directly esterifying temozolomide acid (formula II, 3,4-dihydro-3-methyl-4-oxoimidazo[5,1-d]-1,2,3,5-tetrazine-8-carboxylic acid) with an aliphatic alcohol or an aliphatic thiol in presence of a dehydrate agent to form the compound.

7. Method according to claim 6, wherein the dehydrate agent is selected from DCC, BOP, Pybrop, HBTU, TBTU, TNTU, TSTU, PyBrOP, and HOBt.

8. A pharmaceutical composition comprising a compound of formula (I)

(I)

in which
 X represents oxygen (O) or sulphur (S);
 R represents a $C_5$–$C_{10}$ alkyl, cycloalkyl, alkenyl or alkynyl group, each of the groups being optionally substituted by one or more substituent groups independently selected from halogen atoms, —$OR_1$, —$SR_1$, —$NR_1R_2$, and an optionally substituted phenyl group; and
 $R_1$ and $R_2$ each independently represent a hydrogen atom, or a $C_1$–$C_{10}$ alkyl, cycloalkyl, alkenyl or alkynyl group, in combination with a pharmaceutically acceptable adjuvant, diluent or carrier.

9. A method of treating malignant melanoma by topically or transdermally applying a pharmaceutically effective amount of a compound according to claim 1.

* * * * *